United States Patent
Wilson et al.

(10) Patent No.: US 8,773,500 B2
(45) Date of Patent: Jul. 8, 2014

(54) IN VIVO IMAGE CAPTURING SYSTEM INCLUDING CAPSULE ENCLOSING A CAMERA

(75) Inventors: Gordon Wilson, San Francisco, CA (US); Kang-Huai Wang, Saratoga, CA (US)

(73) Assignee: Capso Vision, Inc., Saratoga, CA (US)

( * ) Notice: Subject to any disclaimer, the term of this patent is extended or adjusted under 35 U.S.C. 154(b) by 1491 days.

(21) Appl. No.: 11/642,275

(22) Filed: Dec. 19, 2006

(65) Prior Publication Data

US 2008/0143822 A1    Jun. 19, 2008

Related U.S. Application Data

(66) Substitute for application No. 60/760,794, filed on Jan. 19, 2006.

(60) Provisional application No. 60/760,079, filed on Jan. 18, 2006.

(51) Int. Cl.
*H04N 7/00* (2011.01)

(52) U.S. Cl.
USPC ............................................................. 348/36

(58) Field of Classification Search
USPC ............................................ 348/36; 600/160
See application file for complete search history.

(56) References Cited

U.S. PATENT DOCUMENTS

| | | | |
|---|---|---|---|
| 4,566,763 A | 1/1986 | Greguss | |
| 5,473,474 A | 12/1995 | Powell | |
| 6,748,797 B2 | 6/2004 | Breed et al. | |
| 6,836,377 B1 | 12/2004 | Kislev et al. | |
| 6,918,872 B2 | 7/2005 | Yokoi et al. | |
| 2002/0109774 A1 | 8/2002 | Meron et al. | |
| 2003/0117491 A1 | 6/2003 | Avni et al. | |
| 2003/0171653 A1 | 9/2003 | Yokoi et al. | |
| 2004/0092825 A1 | 5/2004 | Madar et al. | |
| 2005/0004474 A1 | 1/2005 | Iddan | |
| 2005/0049462 A1 | 3/2005 | Kanazawa | |
| 2005/0143624 A1 | 6/2005 | Iddan | |

(Continued)

FOREIGN PATENT DOCUMENTS

| JP | 2002-233494 | 8/2002 |
|---|---|---|
| JP | 2003-260025 | 9/2003 |

(Continued)

OTHER PUBLICATIONS

Fair, S.B. et al. "Panoramic endoscopy", SPIE vol. 1649 Optical Fibers in Medicine VII (1992), pp. 203-207.

(Continued)

*Primary Examiner* — Robert B Harrell (57) ABSTRACT

An in vivo image capturing system includes a capsule, and a camera encased within the capsule and configured to capture through a transparent window of the capsule, a view outside the capsule. The system includes a light source enclosed within the capsule and a reflector configured to reflect a ray of light from the light source, away from the camera. Wherever incoming image rays and outgoing illuminating light rays intersect at a common point on any surface of the transparent window, an angle between an outgoing illuminating light ray and a surface normal exceeds an angle between an incoming image ray and the surface normal such that a reflection of the outgoing illuminating light ray from said any surface is not within a field of view (FOV) of the camera.

54 Claims, 8 Drawing Sheets

(56) References Cited

U.S. PATENT DOCUMENTS

| | | | |
|---|---|---|---|
| 2005/0143644 | A1 | 6/2005 | Gilad et al. |
| 2005/0146644 | A1 | 7/2005 | Miyazawa et al. |
| 2005/0187433 | A1* | 8/2005 | Horn et al. .................... 600/160 |
| 2006/0178557 | A1 | 8/2006 | Mintchev et al. |
| 2006/0217593 | A1 | 9/2006 | Gilad et al. |

FOREIGN PATENT DOCUMENTS

| | | |
|---|---|---|
| JP | 2005-334647 | 12/2005 |
| WO | WO 95/02841 | 1/1995 |
| WO | WO 2004/032621 | 4/2004 |
| WO | WO 2004/096008 | 11/2004 |
| WO | WO 2005/077253 | 8/2005 |

OTHER PUBLICATIONS

PCT/US06/48752, International Search Report, dated Sep. 3, 2008, pp. 2.
PCT/US06/48752, Written Opinion of the International Searching Authority, dated Sep. 3, 2008, pp. 6.
Chinese $1^{st}$ Office Action, dated Apr. 14, 2010 in Application No. 200680050987.1, pp. 1-7.
Yagi, Y. "Omnidirectional Sensing and Its Applications", IEICE Transactions on Information and Systems. vol. E-82-D, No. 3, Mar. 1999, pp. 568-579.
Lehner, D.L. et al. "Characterization of the Panoramic Annular Lens", Experimental Mechanics, Springer New York LLC, vol. 36, No. 4, Dec. 1996, pp. 333-338.
Chinese $2^{nd}$ Office Action, dated Mar. 24, 2011 in Application No. 200680050987.1, pp. 5.
Extended European Search Report, dated Jul. 16, 2010 in European Patent Application 06849994.6, pp. 9.
First European Office Action dated Sep. 20, 2010 in European Patent Application 06849994.6, pp. 5.
Response to Office Action dated Mar. 21, 2011 in European Patent Application 06849994.6, pp. 31.
Second European Office Action dated May 20, 2011 in European Patent Application 06849994.6, pp. 6.
Response to Office Action dated Sep. 20, 2011 in European Patent Application 06849994.6, pp. 16.
Chinese $3^{rd}$ Office Action, dated Mar. 7, 2012 in Application No. 200680050987.1, pp. 4.
Japanese $1^{st}$ Office Action dated Apr. 17, 2012 in Application No. 2008-551269, pp. 7.
International Preliminary Report on Patentability dated May 15, 2012 in PCT Application PCT/US06/48752 (6 pages).
Applicant's Response dated Jul. 17, 2012 to the $1^{st}$ Office Action in Japanese Patent Application No. 2008-5512699 (8 pages).
Applicant's Response dated Jul. 17, 2012 to the $3^{rd}$ Office Action in Chinese Patent Application No. 200680050987.1, (11 pages).
Applicant's Response dated Jun. 8, 2011 to the $2^{nd}$ Office Action in Chinese Patent Application No. 200680050987.1, (8 pages).
Applicant's Response dated Aug. 17, 2010 to the $1^{st}$ Office Action in Chinese Patent Application No. 200680050987.1, (16 pages).
Applicant's Response dated Sep. 18, 2012 in European Patent Application 06849994.6 (18 pages).
Summons and Preliminary Opinion of Examining Division dated Nov. 19, 2012 in European Patent Application 06849994.6 (12 pages).
EPO, Minutes of oral proceedings, European Patent Application EP06849994.6, Jun. 25, 2013, pp. 10.
Wang, International Publication WO 2007/126429 A2, Jun. 21, 2013, pp. 35.
Applicant's Written Submission in preparation to/during oral proceedings, European Patent Application EP06849994.6, Apr. 19, 2013, pp. 25.
Applicant's Written Submission in preparation to/during oral proceedings, European Patent Application EP06849994.6, Mar. 25, 2013, pp. 18.
Applicant's Response, European Patent Application EP06849994.6, Aug. 27, 2010, pp. 19.
Office Action, Japanese Patent Application 2008-551269, May 7, 2013, pp. 6.
Amended claims filed after receipt of (European) search report in European Patent Application EP06849994.6, Aug. 1, 2008, pp. 17.

* cited by examiner

IN VIVO IMAGE CAPTURING SYSTEM INCLUDING CAPSULE ENCLOSING A CAMERA

PRIORITY CLAIM TO PROVISIONAL APPLICATION

This application claims priority from U.S. Provisional Patent Application No. 60/760,079 filed on Jan. 18, 2006, entitled 'In Vivo Sensor with Panoramic Camera,' and U.S. Provisional Patent Application No. 60/760,794 filed Jan. 19, 2006, entitled 'In Vivo Autonomous Sensor with Onboard Data Storage.'

BACKGROUND

Various autonomous devices have been developed that are configured to capture an image from within in vivo passages and cavities within a body, such as those passages and cavities within the gastrointestinal (GI) tract. These devices typically comprise a digital camera housed within a capsule along with light sources for illumination. The capsule may be powered by batteries or by inductive power transfer from outside the body. The capsule may also contain memory for storing captured images and/or a radio transmitter for transmitting data to an ex vivo receiver outside the body.

A common diagnostic procedure involves the patient swallowing the capsule, whereupon the camera begins capturing images and continues to do so at intervals as the capsule moves passively through the cavities made up of the inside tissue walls of the GI tract under the action of peristalsis. The capsule's value as a diagnostic tool depends on it capturing images of the entire interior surface of the organ or organs of interest. Unlike endoscopes, which are mechanically manipulated by a physician, the orientation and movement of the capsule camera are not under an operator's control and are solely determined by the physical characteristics of the capsule, such as its size, shape, weight, and surface roughness, and the physical characteristics and actions of the bodily cavity. Both the physical characteristics of the capsule and the design and operation of the imaging system within it must be optimized to minimize the risk that some regions of the target lumen are not imaged as the capsule passes through the cavity.

Figure 1:
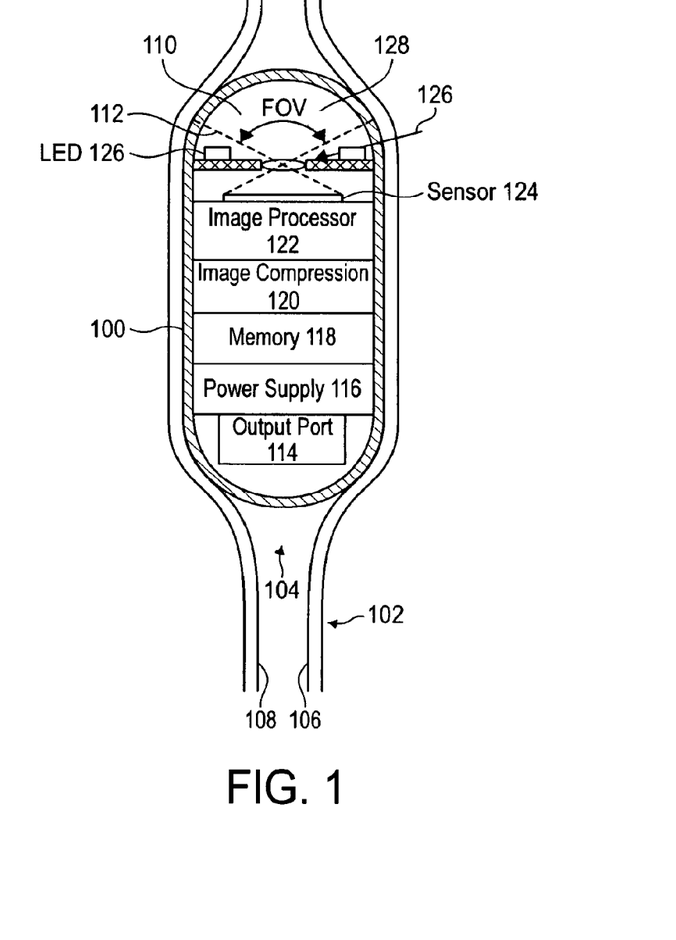
FIG. 1 illustrates the field of view of a capsule camera in the small intestine.

Two general image-capture scenarios may be envisioned, depending on the size of the organ imaged. In relatively constricted passages, such as the esophagus and the small intestine, a capsule which is oblong and of length less than the diameter passage, will naturally align itself longitudinally within the passage. Typically, the camera is situated under a transparent dome at one (or both) ends of the capsule. The camera faces down the passage so that the center of the image comprises a dark hole. The field of interest is the intestinal wall at the periphery of the image The capsule 100 is encased in a housing 101 so that it can travel in vivo inside an organ 102, such as an esophagus or a small intestine, within an interior cavity 104. The capsule may be in contact with the inner surfaces 106, 108 of the organ, and the camera lens opening 110 can capture images within its field of view 112. The capsule may include an output port 114 for outputting image data, a power supply 116 for powering components of the camera, a memory 118 for storing images, image compression 120 circuitry for compressing images to be stored in memory, an image processor 122 for processing image data, and LEDs 126 for illuminating the surfaces 106, 108 so that images can be captured from the light that is scattered off of the surfaces.

It is desirable for each image to have proportionally more of its area to be intestinal wall and proportionally less the receding hole in the middle. Thus, a large FOV is desirable. A typical FOV is 140°. Unfortunately, a simple wide-angle lens will exhibit increased distortion and reduced resolution and numerical aperture at large field angles. High-performance wide-angle and "fish-eye" lenses are typically large relative to the aperture and focal length and consist of many lens elements. A capsule camera is constrained to be compact and low-cost, and these types of configurations are not cost effective. Further, these conventional devices waste illumination at the frontal area of these lenses, and thus the power use to provide such illumination is also wasted. Since power consumption is always a concern, such wasted illumination is a problem. Still further, since the intestinal wall within the filed of view extends away from the capsule, it is both foreshortened and also requires considerable depth of field to image clearly in its entirety. Depth of field comes at the expense of exposure sensitivity.

The second scenario occurs when the capsule is in a cavity, such as the colon, whose diameter is larger than any dimension of the capsule. In this scenario the capsule orientation is much less predictable, unless some mechanism stabilizes it. Assuming that the organ is empty of food, feces, and fluids, the primary forces acting on the capsule are gravity, surface tension, friction, and the force of the cavity wall pressing against the capsule. The cavity applies pressure to the capsule, both as a passive reaction to other forces such as gravity pushing the capsule against it and as the periodic active pressure of peristalsis. These forces determine the dynamics of the capsule's movement and its orientation during periods of stasis. The magnitude and direction of each of these forces is influenced by the physical characteristics of the capsule and the cavity. For example, the greater the mass of the capsule, the greater the force of gravity will be, and the smoother the capsule, the less the force of friction. Undulations in the wall of the colon will tend to tip the capsule such that the longitudinal axis of the capsule is not parallel to the longitudinal axis of the colon.

Also, whether in a large or small cavity, it is well known that there are sacculations that are difficult to see from a capsule that only sees in a forward looking orientation. For example, ridges exist on the walls of the small and large intestine and also other organs. These ridges extend somewhat perpendicular to the walls of the organ and are difficult to see behind. A side or reverse angle is required in order to view the tissue surface properly. Conventional devices are not able to see such surfaces, since their FOV is substantially forward looking. It is important for a physician to see all areas of these organs, as polyps or other irregularities need to be thoroughly observed for an accurate diagnosis. Since conventional capsules are unable to see the hidden areas around the ridges, irregularities may be missed, and critical diagnoses of serious medical conditions may be flawed. Thus, there exists a need for more accurate viewing of these often missed areas with a capsule.

Figure 2:
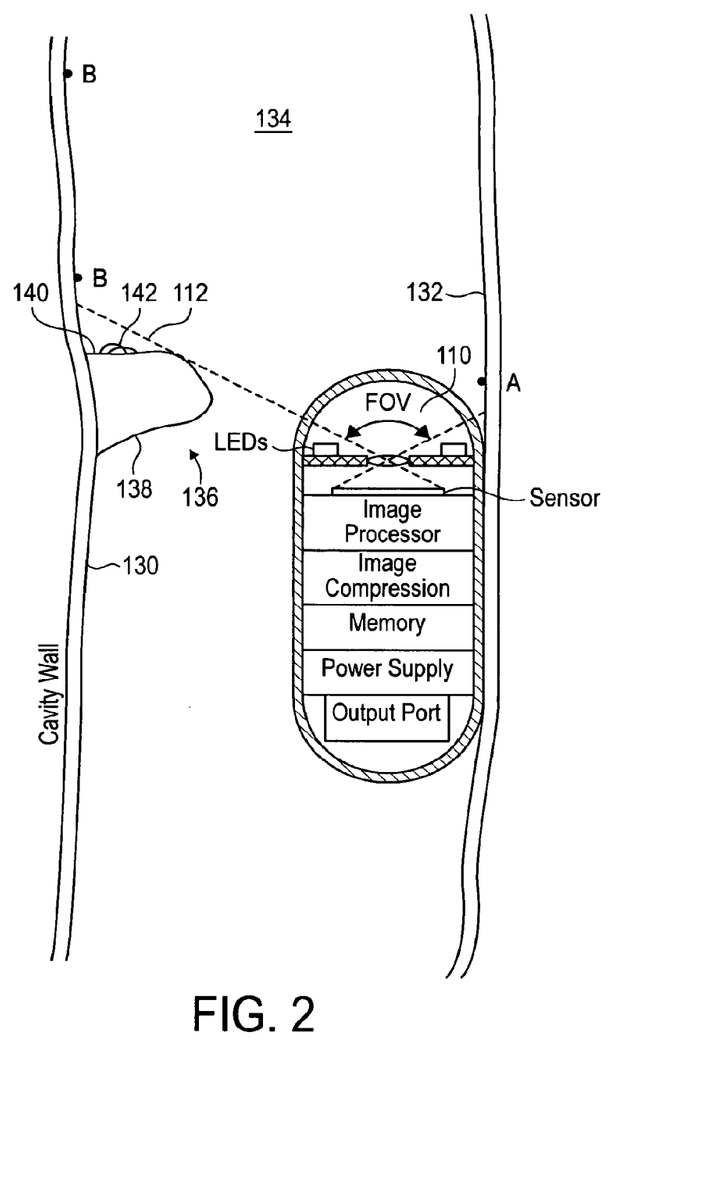
FIG. 2 illustrates the field of view of a capsule camera in the large intestine.

FIG. 2 shows a relatively straightforward example where the passage 134, such as a human colon, is relatively horizontal, with the exception of the ridge 136, and the capsule sits on its bottom surface 132 with the optical axis of the camera parallel to the colon longitudinal axis. The ridge illustrates a problematic viewing area as discussed above, where the front surface 138 is visible and observable by the capsule 100 as it approaches the ridge. The backside of the capsule 140, however, is not visible by the capsule lens, as the limited FOV 110 does not pick up that surface. Specifically, the range 110 of the FOV misses part of the surface, and moreover misses the irregularity illustrated as polyp 142.

Three object points within the field of view 110 are labeled A, B, and C. The object distance is quite different for these three points, where the range of the view 112 is broader on one side of the capsule than the other, so that a large depth of field is required to produce adequate focus for all three simultaneously. Also, if the LED (light emitting diode) illuminators provide uniform flux across the angular FOV, then point A will be more brightly illuminated than point B and point B more than point C. Thus, an optimal exposure for point B results in over exposure at point A and under exposure at point C. For each image, only a relatively small percentage of the FOV will have proper focus and exposure, making the system inefficient. Power is expended on every portion of the image by the flash and by the imager, which might be an array of CMOS or CCD pixels. Moreover, without image compression, further system resources will be expended to store or transmit portions of images with low information content. In order to maximize the likelihood that all surfaces within the colon are adequately imaged, a significant redundancy, that is, multiple overlapping images, is required.

One approach to alleviating these problems is to reduce the instantaneous FOV but make the FOV changeable. Patent application 2005/0146644 discloses an in-vivo sensor with a rotating field of view. The illumination source may also rotate with the field of view so that regions outside the instantaneous FOV are not wastefully illuminated. This does not completely obviate the problem of wasteful illumination, and furthermore creates other power demands when rotating. Also, this innovation by itself does not solve the depth of field and exposure control problems discussed above.

Thus there exists a need in the art for a more improved system and method for in-vivo viewing of organs with a capsule, where better viewing angles can provide better observations of tissue surfaces. As will be seen below, the invention provides such a system and a method that overcomes the problems of the prior art, and they do so in an elegant manner.

SUMMARY

An in vivo image capturing system includes a capsule, and a camera encased within the capsule and configured to capture through a transparent window of the capsule, a view outside the capsule. The system includes a light source enclosed within the capsule and a reflector configured to reflect a ray of light from the light source, away from the camera. Wherever incoming image rays and outgoing illuminating light rays intersect at a common point on any surface of the transparent window, an angle between an outgoing illuminating light ray and a surface normal exceeds an angle between an incoming image ray and the surface normal such that a reflection of the outgoing illuminating light ray from said any surface is not within a field of view (FOV) of the camera.

DETAILED DESCRIPTION OF PREFERRED EMBODIMENTS

We present a capsule camera that utilizes a panoramic camera. Panoramic cameras provide a FOV that exceeds 180° but with an obscuration at the center of the FOV. For example the FOV might be a full 360° of latitude with angles of longitude ranging from 160° to 200°. Panoramic annular lenses are first described in U.S. Pat. No. 4,566,763, and refinements are described in U.S. Pat. No. 5,473,474. The panoramic FOV reduces the possibility that the camera will fail to image some portion of the organ as it passes through it, even if its orientation is variable. We also disclose the use of a balloon or balloons attached to the capsule that position the capsule near the center of a cavity, such as the colon, whose diameter is larger than that of the capsule, and maintain a longitudinal capsule orientation. The walls of the colon within the panoramic FOV are then nearly equidistant from the camera, reducing the required depth of field and simplifying exposure.

The invention is directed to a panoramic in vivo camera system. In one embodiment, the system is configured in a capsule, and a panoramic camera is encased within the capsule and configured to capture a panoramic view of tissue surface around or otherwise about the capsule. An optical system is configured to illuminate an area of interest outside the capsule to the camera system. More generally, the invention provides a remote image capturing system that includes a housing that acts as a delivery system such as a capsule for example. This housing encloses the remote image capturing system for function and protection. A camera is enclosed within the housing and is configured to capture a panoramic image of an environment immediately surrounding the housing, such as within a subject's esophagus, large or small intestine, or other organ. A light source is also included to provide an illumination source for the camera. At least one power source can be electronically coupled with the light source and the processing system to provide power to each.

The optical system may include a transparent window for exposing an image onto the panoramic camera. The panoramic camera can be configured with a longitudinal field of view and a latitudinal field of view, where that the camera is configured to capture a panoramic image of an organ.

In one embodiment, the invention is directed to an in vivo image capturing system, where the system includes a camera having an entrance pupil, the camera configured to capture a panoramic image of an environment surrounding the camera, wherein the panoramic image is captured on a single image plane. The system further includes a light source for providing an illumination source for the camera and a closed housing for enclosing the camera and the light source. The system may further comprise a power source for providing power to the light source and the camera, and the power source may be a battery located within the capsule. The power source may be an inductive power source located outside the capsule and configured to induce power into the capsule to power the camera and illumination source. The closed housing may include a transparent window for passing light into the panoramic camera, wherein the panoramic camera is configured with a longitudinal field of view defined by a range of view angles relative to a longitudinal axis of the capsule and a latitudinal field of view defined by a panoramic range of azimuth angles about the longitudinal axis such that the camera can capture a panoramic image covering substantially a 360 deg latitudinal FOV and a longitudinal FOV ranging from some angle greater than 0 deg to another angle greater than 90 deg.

The camera may have a longitudinal axis such that the angular FOV includes a plane substantially in its entirety, wherein the plane is perpendicular to the axis and intersects the pupil. The system may include an optical system that has a panoramic annular lens configured to focus an image onto the single image plane. The capsule may be configured with a body of oblong shape and having a longitudinal axis along the length of the body, the system further including an optical system having a panoramic annular lens that enables images to be captured by the panoramic camera radially about the longitudinal axis and onto the single image plane. The camera may be oriented within the capsule to capture images radially about the longitudinal axis and has a FOV that is substantially perpendicular with respect to the capsule to enable viewing of a tissue surface oriented parallel to the principle direction of travel of the capsule and to enable capturing an image of the tissue surface onto the single image plane. The capsule may have a housing that is oblong in shape, and wherein the camera is oriented within the housing to capture images radially about the longitudinal axis and along the axis of the body, the system further including an optical system having a panoramic annular lens and a window located substantially surrounding area of the oblong body for receiving light rays from an object into the panoramic annular lens. The longitudinal axis may be a concentric axis of symmetry for the panoramic annular lens.

The panoramic annular lens may have a concentric axis of symmetry and includes two refractive surfaces and two reflective surfaces configured to allow incoming light to pass through a first refractive surface into a transparent medium. Alternatively, the panoramic annular lens may have a concentric axis of symmetry and includes two refractive surfaces and two reflective surfaces configured to allow incoming light to pass through a first refractive surface into a transparent medium, to be reflected by a first reflective surface, then reflected by a second reflective surface, and then to exit the medium through a second refractive surface. The panoramic annular lens may be configured to produce an image with a cylindrical field of view from a point-of-view on the concentric axis. The reflective and refractive surfaces may be conicoid surfaces of revolution, and wherein the conic constant of the first reflector is in the range of −0.6 to +2. The reflective and refractive surfaces may also be conicoid surfaces of revolution, wherein the conic constant of the first reflective surface is in the range of −0.6 to +2, where the conic constant of the second reflective surface is chosen to be less than that of the first. The reflective and refractive surfaces may be one of conicoid surfaces of revolution, spheroidal surfaces, or aspheroidal surfaces.

The system may include further a data processor configured to generate a continuous image made up of multiple captured images. The data processor may be located outside the capsule. The data processor may be configured to generate a continuous image made up of multiple contiguous captured images. The system may further include a memory configured to store captured images, where the memory is an electronic memory, or other type of memory. The memory may be located within the capsule. The memory may be located within the capsule, wherein the processor is configured to compress image data and to store the compressed image data in the electronic memory.

The memory may be located outside the capsule, wherein image data is stored in the memory for subsequent processing, and the system may further comprise a remote processor configured to compress image data and to store the compressed image data in the memory.

The system may further include a transmission module configured to transmit images captured by the panoramic camera to a remote receiver configured to receive captured images. The transmission module may be configured to transmit images captured by the panoramic camera to a remote receiver having data storage configured to store captured images for processing by an image processor.

In operation, the system may perform a method of in-vivo imaging, by providing a device for panoramic in-vivo imaging of the gastrointestinal tract onto a single image plane. The method further includes emitting electromagnetic radiation from the capsule; and receiving reflections of the electromagnetic radiation from tissue surfaces for use in forming a panoramic image of the tissues from a field of view that includes substantially all directions perpendicular to the principle direction of travel through the gastrointestinal tract.

The method may further include uploading the compressed image data to a host computer for processing, and it may first perform compression on images detected by an image sensor to produce compressed image data. The process may further include performing compression on images detected by an image sensor in the capsule to produce compressed image data, storing the compressed image data in a memory in the capsule, then uploading the compressed image data to a host computer. The step of uploading the images to a host computer may further comprise retrieving the capsule housing and uploading the images by connecting the capsule to the host computer. Uploading the images to a host computer may further comprise uploading the images by transmitting the images from the capsule to the host computer.

In a wireless system the method may further include uploading the compressed image data to a host computer with a wireless signal. And the method may also perform compression on images detected by an image sensor to produce compressed image data, and then upload the compressed image data to a host computer via a wireless communication signal. The method may perform the process by performing compression on images detected by an image sensor in the capsule to produce compressed image data, storing the compressed image data in a memory in the capsule; and then uploading the compressed image data to a host computer via a wireless communication signal. More specifically, the method for in-vivo imaging with a camera encased within a capsule may include providing a capsule housing having a portion at least partially transparent to electromagnetic radiation in a given wavelength range, ingesting said capsule by a patient, emitting electromagnetic radiation in said wavelength range from said capsule, detecting images from reflections of said electromagnetic radiation with an image sensor using a panoramic camera, performing compression on images detected by an image sensor in said capsule before storing said images in a transistor memory in said capsule, retrieving said capsule from said patient, and then uploading said images to a host computer.

In yet another embodiment, the invention provides a capsule configured to house a camera for in vivo imaging, where the capsule includes a panoramic camera and an illuminating light source. The capsule may be a closed capsule having a first set of inner and outer transparent window surface regions demarcated by the intersections of incoming image rays within the camera FOV with the interior and exterior surfaces of the window and a second set of inner and outer transparent window surface regions demarcated by the intersections of illuminating light rays, passing from within the capsule to the exterior, with the interior and exterior surfaces of the window; wherein the inner surface regions from each set and the outer surface regions from each set are sufficiently non-overlapping such that wherever incoming image rays and outgoing illuminating rays intersect at a common point on a window surface the angle between the outgoing ray and the surface normal exceeds the angle between the incoming ray and the surface normal such that the reflection of the outgoing ray from the surface is not within the camera FOV. The inner surface regions from each set may be non-overlapping. Alternatively, the outer surface regions from each set are non-overlapping. The capsule may further include a reflector configured to reflect illuminating light from the illuminating light source away from the camera and toward a subject surface. The camera may include a lens configured to receive illuminating light reflected from a subject surface, the capsule having a reflector configured to reflect illuminating light from the illuminating light source away from the camera in a manner that prevents stray light from directly entering the camera lens without being scattered by a subject surface.

Figure 3A:
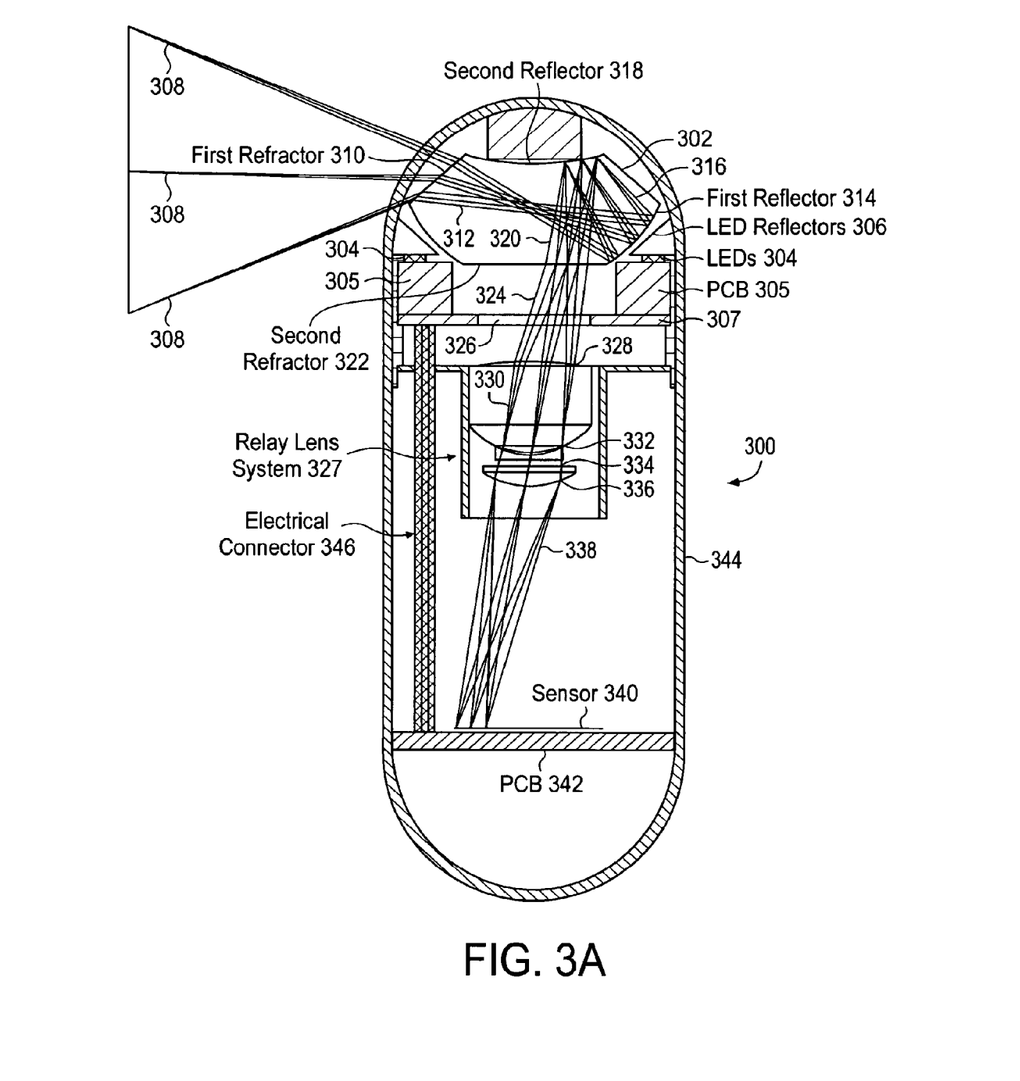
FIGS. 3a-b illustrates the panoramic annular lens (PAL) in an endoscopic capsule.

Another embodiment of a capsule camera 300 having a panoramic annular lens (PAL) 302, is shown schematically in FIG. 3a. The lens 302 has a concentric axis of symmetry and comprises two refractive surfaces and two reflective surfaces such that incoming light passes through the first refractive surface into a transparent medium, is reflected by the first reflective surface, then by the second reflective surface, and then exits the medium through the second refractive surface.

The capsule camera 300 includes LED outputs 304 configured to illuminate outside the capsule onto a subject, such as tissue surface being imaged. The LEDs include LED reflectors 306 configured to reflect any stray LED light away from the lens 302. The purpose of the LED light rays is to reflect off of the tissue surface ant into the lens 302 so that an image can be recorded. The reflectors serve to reflect any light from the light source, the LEDs, away from the lens 302 so that only light rays reflected from the tissue surface will be imaged. The LEDs are connected to printed circuit boards PCBs 305 that are connected to each other via a conductor wire or plate 307, distributing power to each LED. The lens 302 is configured to receive and capture light rays 308 that are reflected off of an outside surface, such as a tissue surface, and receives the reflected rays through a first refractor 310. The refracted rays 312 are transmitted to a first reflector 314, which transmits reflected rays 316 onto the surface of a second reflector 318. The second reflector then reflects reflected rays 320 through a second refractor 322, sending refracted rays 324 through opening 326 and into a relay lens system 327.

The system shown is a Cooke triplet relay lens, and it includes a first lens 328 for receiving the refracted rays 324 from the second refractor 322. The first lens focuses the light rays 330 onto a second lens 332. Those focused rays 334 are sent to third lens 336, which focuses rays 338 onto sensor 340. The sensor is mounted on PCB 342, which is connected to the capsule outer walls 344.

The capsule 300 further includes electrical conductor 346 connecting the PCB 342 holding the sensor to the conductor plate or wire 307. The electrical conductor 346 is configured for powering the LEDs 304 through the conductor plate 307 and PCBs 305 that hold the LEDs 304. Those skilled in the art will understand that other configurations are possible without departing from the spirit and scope of the invention, which is defined by the appended claims.

The PAL lens 302 produces an image with a cylindrical FOV from a point-of-view on the concentric axis. The surfaces of the lens 302 may be conicoid surfaces of revolution, or they may be other spheroidal or aspheroidal shapes. In a preferred embodiment, the conic constant of the first reflector is optimally in the range of −0.6 to +2 with the conic constant of the second reflector chosen to be less than that of the first. For example, the first reflector might be ellipsoidal with the second reflector hyperboloidal.

A relay image system after the PAL lens 302 forms an image on a two-dimensional light sensor 340 that may be a commonly known sensor such as a CMOS or CCD array. FIG. 3a illustrates a Cooke triplet relay lens 327. There exists other configurations that are well known in the art and include double-Gauss configurations.

Figure 3B:
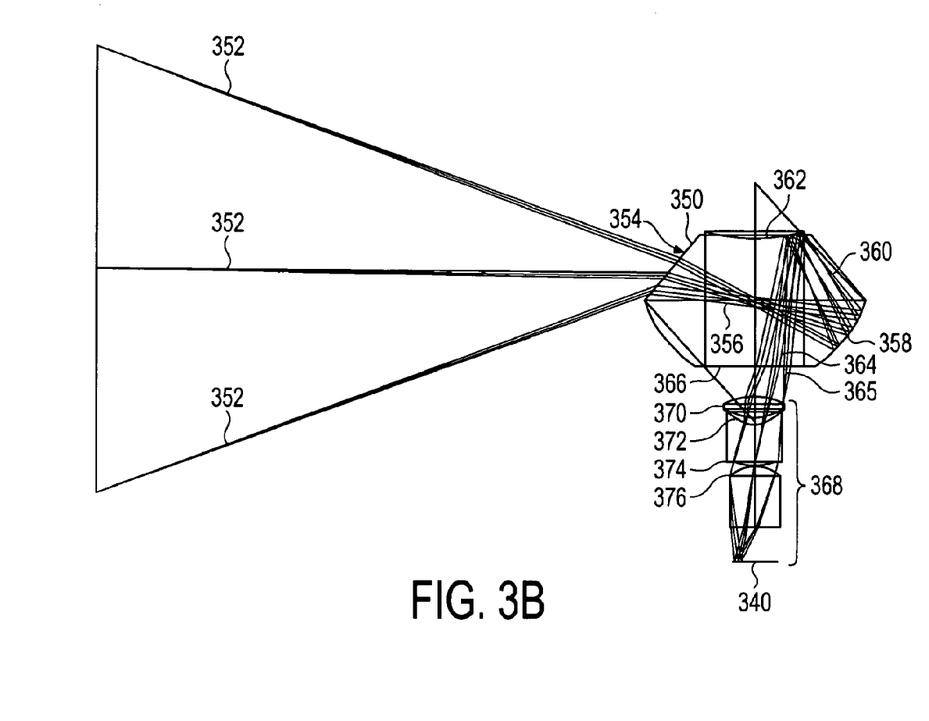

Referring to FIG. 3b, a lens design is shown a lens design 350 with reduced total track length for the relay imaging system. The lens 350 is configured to receive and capture light rays 352 that are reflected off of an outside surface, such as a tissue surface, and receives the reflected rays through a first refractor 354. The refracted rays 356 are transmitted to a first reflector 358, which transmits reflected rays 360 onto the surface of a second reflector 362. The second reflector then reflects reflected rays 364 through a second refractor 366, sending refracted rays 365 through opening 326 and into a relay lens system 368. The relay lens system is configured with lenses 370, 372, 374, 376 for focusing the light rays onto sensor 340. The reduced total track of the imaging system allows for more compact design and manufacture of a camera inside the imaging capsule, providing for different designs and configurations.

In either embodiment illustrated in FIG. 3a or 3b, the capsule camera may instead use other panoramic lens designs including those that utilize a single reflector in the shape of a paraboloid, spheroid, cone, or tetrahedron, in conjunction with relay lenses, to map a cylindrical FOV onto an image plane. Other designs may utilize a single concave ellipsoidal reflector.

Referring again to FIG. 3a, this figure illustrates the PAL lens 302 in an endoscopic capsule. The capsule is shown as a cylinder with hemispherical ends. In a preferred embodiment, at least a circumferential band of the capsule housing must be transparent to allow illuminating light to exit the capsule and to allow image light to enter the capsule. In a preferred embodiment, the optical axis of the lens is oriented along the longitudinal axis of a cylinder (FIG. 4) or along the major axis of an ellipsoid in an ellipsoid capsule configuration.

Figure 4:
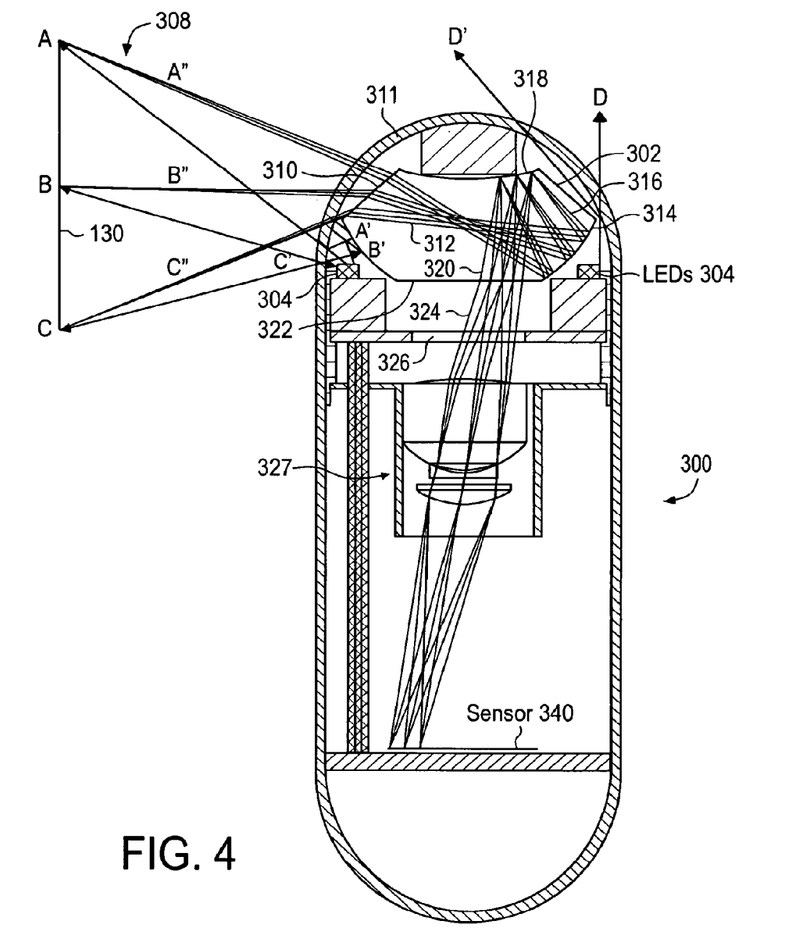
FIG. 4 illustrates a capsule with the optical axis of the lens oriented along the longitudinal axis of a cylinder.

Referring to FIG. 4, the LED 304 is configured to emit light rays A, B, C on a subject surface 130, such as tissue surface. The capsule wall 311 would be transparent to the incoming rays A", B", C", which are each received through the first refractor 310. The LED light rays A', B', C' are reflected off of the lens 302, so that the LED rays do not distort the image captured by the sensor 340.

Just as discussed above, the lens 302 is configured to receive and capture light rays 308 that are reflected off of an outside surface, such as a tissue surface, and receives the reflected rays through a first refractor 310. The refracted rays 312 are transmitted to a first reflector 314, which transmits reflected rays 316 onto the surface of a second reflector 318. The second reflector then reflects reflected rays 320 through a second refractor 322, sending refracted rays 324 through opening 326 and into a relay lens system 327.

The capsule might have any oblong shape or a spherical shape, however, and the optical axis may have any orientation within the capsule. Any electrical connections made from the end of the lens above the $2^{nd}$ reflector to the region below the $1^{st}$ reflector will obscure the field of view to some extent. The sensor is necessarily below the lens. Thus, electronics placed above the lens and the sensor cannot share a common power supply and control circuitry without obscuring connecting wires. Therefore, it is advantageous to place the lens with the second reflector adjacent to one end of the capsule. The quasi-spherical shape of the PAL fits economically within the hemispherical end of the capsule, as well. However, if a balloon is attached to the end of the capsule above the lens, it may be desirable to lower the lens so that the balloon is not in the FOV. If batteries are placed above the lens, electrical connections can be made from above to below the lens with minimal vignetting if the wires are thin or of a transparent conductive material such as indium oxide.

Referring again to FIG. 3a, Light-emitting diode (LED) illumination sources sit on a multilayer printed circuit board (PCB) outside the PAL and below the first refractive surface. LEDs are attractive sources due to their low cost, efficiency, compactness, and low coherence (which prevents speckle). Other illumination sources such as laser, incandescent, arc, or fluorescent sources are conceivable as well. Color photographs require a white light source. White LEDs are available that may include a blue or violet LED along with phosphorescent materials that are excited by the LED and emit photons at longer wavelengths. A white light source may comprise a combination of LEDs or lasers emitting at different colors, such as red, green, and blue, within the visible spectrum and that together produce the same spectral response from the sensor (which has pixels sensitive to particular bands of color) as would a continuous-spectrum white light source.

The PCB that holds the LEDs may also serve as a mount for the LED and a baffle and or aperture stop for the relay lens. Alternatively, structures that perform these functions, along with the relay-lens barrel may attach to or support the PCB. LED drive circuits may be situated on the same PCB or on another PCB. Either way, control signals must be passed to the LEDs. Thus, some form of electrical connection between the LED-PCB and another PCB, for example the PCB that holds the sensor, is required. This connector might be a flexible PCB, a series of conductive pins or wires, or some other form of connector.

A potential problem with a capsule camera is that illumination light reflected by the exterior and interior surfaces of the capsule body may impinge on the sensor. Antireflection coatings can reduce these reflections, although adding these coatings to the capsule adds cost to the system. The correct geometry, however, ensures that the reflections will not overlap with the image on the sensor. U.S. Pat. No. 6,836,377 and U.S. Pat. No. 6,918,872 disclose two such geometries for non-panoramic capsule cameras. In the first, the capsule dome is ellipsoidal with the sensor at its center and the LEDs lying on the focal curve. In the second, the dome is spherical with the sensor at the middle and the LEDs in the same plane further toward the edge of the sphere.

Figure 5:
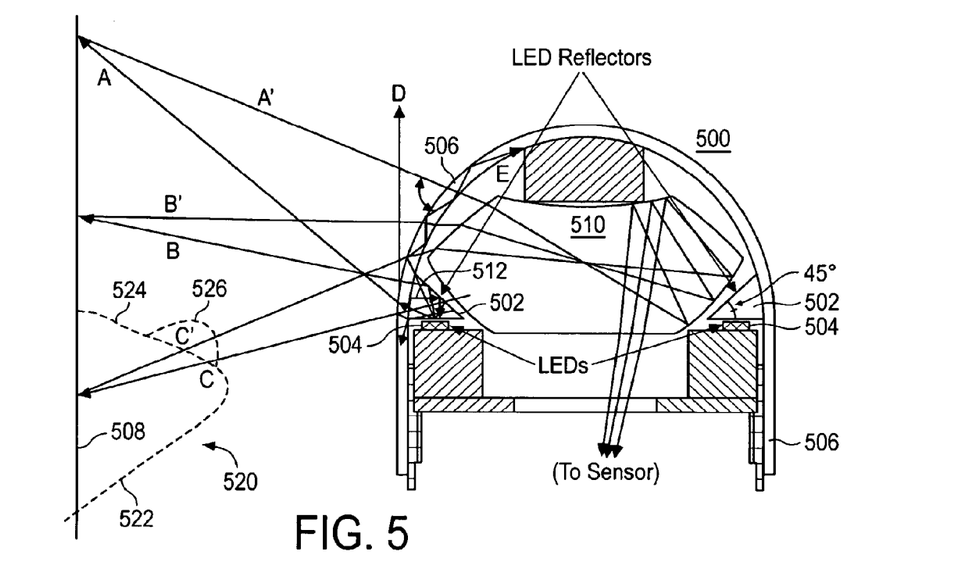
FIG. 5 illustrates a geometry for a panoramic camera where the LEDs lie below and to the outside of the first reflector.

FIG. 5 illustrates a geometry for a panoramic capsule camera where the LEDs lie below and to the outside of the first reflector. A reflective prism 502 sits above each LED 504 with one face of the prism at an angle roughly 45° relative to the longitudinal axis. This face may be coated with a metal or dielectric reflective coating that reflects light from the LED to the object or subject surface. In one embodiment, rather than use a separate prism for each LED, a continuous ring of triangular cross section may be formed into a single reflector 502. In preferred embodiment, the ring is made of a material whose refractive index is nearly the same as that of the capsule housing 506, and an index matching adhesive may be used to bond it to the housing such that reflections at the interface between the ring and the housing are minimized. The figure shows rays A, B, and C passing from the LED 504 to the intestinal wall 508. Scattered light travels along paths A', B', and C' and is collected by lens 510 and imaged on the sensor (not shown). Reflections 512 will occur at the outer surface of the capsule. However, these reflections, shown as dotted lines, reflect back into the prism (or ring) and cannot be collected by the lens.

Still referring to FIG. 5, two additional rays D and E are also shown. Ray D is light from reflector 502 and is refracted at an acute angle and would illuminate the intestinal wall within the field of view if the wall were closer. The reflection of ray D also passes back into the ring. Ray E clears the top of the ring. However, its angle of incidence upon the outer wall of the housing exceeds the critical angle for total internal reflection. The wall of the capsule serves as a light pipe that contains reflected light where much of it will scatter off the block positioned between the second reflector and the top of the capsule and away from the lens.

Also shown in FIG. 5 is a ridge 520. As discussed in the background, such a ridge causes problems in viewing when using conventional devices, where prior art capsules can view and observe front side 522 as the capsule approaches the ridge, but misses the backside 524 because of a limited FOV. Polyp 526 or the area behind the polyp would normally be unobservable by a conventional device. In contrast, the invention provides a more useful and accurate means for observing the backside 524 and polyp 526, where the camera is able to view these surfaces, such as by ray C as illustrated. Ray C is then reflected as Ray C' that returns to the camera through the capsule shell and into lens 510. Thus, the invention provides a very useful and effective means to better observe these remote surfaces that were formerly not visible by prior art capsule cameras.

Figure 6:
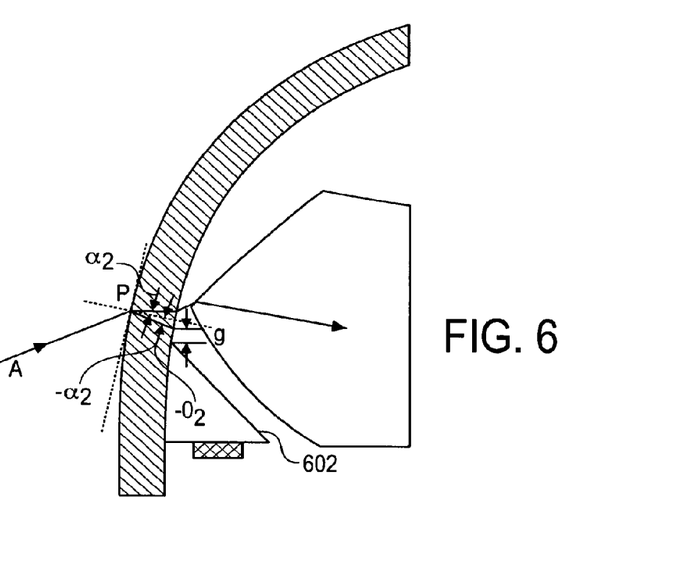
FIG. 6 illustrates the ray paths on entering a capsule.

In FIG. 6, ray A enters the capsule at point P at the largest field angle that the camera's aperture will capture. Within the body of the housing the ray makes an angle $\alpha_2$ with respect to the surface normal. If no rays can pass from the LED to point P at an angle less than or equal to $\alpha_2$, then no reflected LED light from the housing outer wall will enter the camera aperture. As long as the distance g between the apex of the prism and the intersection of a line segment between point P, at an angle $-\alpha_2$ with the surface normal, and the inner wall of the housing, then this condition is satisfied, regardless of the exact position of the LED below the prism.

Figure 7:
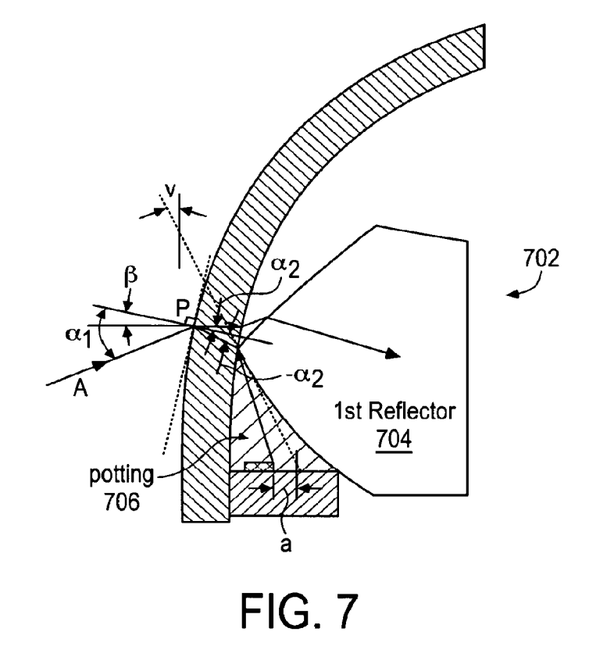
FIG. 7 illustrates another embodiment of panoramic capsule camera and LED illuminators where the region between the LED, the housing, and the outside of the first reflector is filled with an index-matching potting material.

FIG. 7 illustrates a similar embodiment of panoramic capsule camera 702 and LED illuminators 704. In this case, the region between the LED, the housing, and the outside of the first reflector is filled with an index-matching potting material 706. This region serves essentially the same illuminator function as the prism or ring 602 in the FIG. 6. However, this approach eliminates the gap g of FIG. 6. Ray A enters the capsule at point P at the largest field angle that is captured by the camera's aperture. The ray makes an angle $\alpha_1$ with the housing surface normal. The surface normal is at an angle $\beta$ with respect to the horizontal. Ray A makes an angle $\alpha_2$ with respect to the surface normal within the housing wall where n $\sin \alpha_2 = \sin \alpha_1$ and n is the housing index of refraction. A ray emitted by the LED and reflects from the far end of the $1^{st}$ reflector, passes into the housing and intersects the outer wall at point P. If this ray makes an angle of $-\alpha_2$ with the surface normal, then its reflection from the wall will be within the camera FOV. To ensure that no such rays exist, the LED must be placed a distance α or greater away from the intersection of a line tangent to the first reflector at its outermost edge and the plane of the LED emitting surface. One can show that $$a = h[\cot(\gamma) - \cot(2\gamma - \alpha_2 - \beta)]$$

where h is the distance from the LED plane to the ray-reflector intercept and γ is the angle the tangent line makes with the LED plane.

Figure 8:
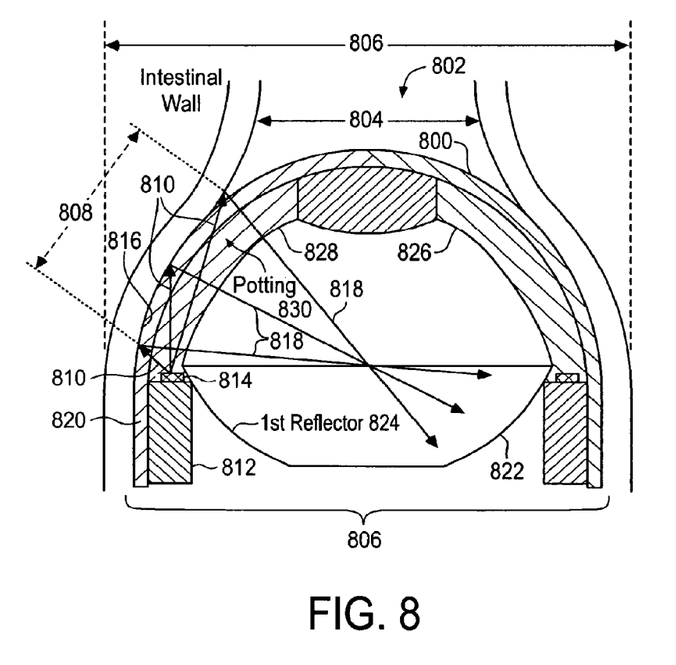
FIG. 8 further illustrates the ray paths for the embodiment of FIG. 7.

Referring to FIG. 8, a panoramic capsule camera 800 is illustrated for imaging the small intestine or other organ having a cavity 802 that has a diameter 804 that is of comparable or smaller diameter to that of the capsule diameter 806. If comparable in diameter, then the capsule would fit close to the walls of the cavity. Thus, the cavity wall touches or is close to the outer wall of the capsule. If the diameter of the cavity is smaller that that of the capsule, the capsule would cause the inside surface of the cavity to expand around and against the capsule as it passes through the cavity. In the embodiment illustrated, the input pupil is the area 808 where light rays 810 are produced from the LED source 812 at output 814 and are reflected from the inner wall 816 of the cavity to enter back into the capsule as reflected rays 818. In this embodiment, the pupil 808 of the panoramic camera 808 is positioned at or near the center of curvature of the hemispherical or similarly shaped transparent capsule end dome 820. The LED output 814 is positioned such that light rays 810 emitted from the LED output 814 do not enter back into the camera in a manner that would reflect the LED rays 810 onto the first reflectors 822, 824, then onto the surfaces 826, 828 of second reflectors respectively and onto a sensor (not shown in FIG. 8). Thus, any LED light reflected from either the inner or outer surfaces of the capsule are not collected by the camera input pupil and are not transmitted to the sensor to distort or otherwise affect the quality of the captured image. Optionally, index-matching potting adhesive 830 may be placed between the camera lenses reflective surfaces 828, 826 and the capsule housing 820. Or, the lenses themselves may fit snuggly against the capsule housing with little or no gap between them. Still referring to FIG. 8, the embodiment shows light LED rays 810 scattered by and reflected from the surface of the intestinal wall from various illuminating rays passing through the input pupil 808.

The invention may be implemented, for example, by having the image processing functions configured as a software application (as an operating system element), a dedicated processor, or a dedicated processor with dedicated code. There may be a small dedicated processor located within the capsule to perform limited functions in conjunction with a sensor to capture and transmit images. In one embodiment, the processor may be a simple logic circuit, dedicated microprocessor, integrated circuit, or other such processor configured to simply transmit image signals to a remote location, such as a proximally located receiver configured to receive the image signals embodying image data. From there, the image data can be stored, processed, forwarded, uploaded to another processor, or otherwise used.

The image data may be first compressed within the capsule, where a smaller amount of data can be transmitted to a remote location. This would reduce the power needed to transmit the information. The invention is directed to capturing a panoramic image by the capsule. Thus, the amount of information transmitted may be substantial, and compression of such data may be desired to reduce the amount transmitted. Transmission requires a good deal of power, and power conservation is very important. Thus, reducing the amount of transmitted date by compression prior to transmission may be desired. Many compression techniques are well known to those skilled in the art, and the invention is not limited to any particular method or technique.

The software executes a sequence of machine-readable instructions, which can also be referred to as code. These instructions may reside in various types of signal-bearing media. In this respect, one aspect of the present invention concerns a program product, comprising a signal-bearing medium or signal-bearing media tangibly embodying a program of machine-readable instructions executable by a digital processing apparatus to perform methods of processing and other functions related to the invention described above.

This signal-bearing medium may comprise, for example, memory located in the capsule, memory in a host computer or in a server, depending on the particular configuration. The memory may be non-volatile storage, a data disc, or even memory on a dedicated server or vendor server for downloading to a processor for installation. Alternatively, the instructions may be embodied in a signal-bearing medium such as the optical data storage disc. Alternatively, the instructions may be stored on any of a variety of machine-readable data storage mediums or media, which may include, for example, a "hard drive", a RAID array, a RAMAC, a magnetic data storage diskette (such as a floppy disk), magnetic tape, digital optical tape, RAM, ROM, EPROM, EEPROM, flash memory, magneto-optical storage, paper punch cards, or any other suitable signal-bearing media including transmission media such as digital and/or analog communications links, which may be electrical, optical, and/or wireless. As an example, the machine-readable instructions may comprise software object code, compiled from a language such as "C++".

Additionally, the program code may, for example, be compressed, encrypted, or both, and may include executable files, script files and wizards for installation, as in Zip files and cab files. As used herein the term machine-readable instructions or code residing in or on signal-bearing media include all of the above means of delivery.

While the foregoing disclosure shows a number of illustrative embodiments of the invention, it will be apparent to those skilled in the art that various changes and modifications can be made herein without departing from the scope of the invention as defined by the appended claims. Furthermore, although elements of the invention may be described or claimed in the singular, the plural is contemplated unless limitation to the singular is explicitly stated.

We claim:

1. An in vivo image capturing system comprising:
a panoramic camera with a field of view (FOV) exceeding 180 degrees;
a capsule enclosing the panoramic camera, the capsule comprising a transparent window configured to pass light into the panoramic camera, the transparent window having an interior surface and an exterior surface;
a light source enclosed within the capsule;
a reflector configured within the capsule to reflect a ray of light from the light source, away from the panoramic camera;
wherein wherever incoming image rays and outgoing illuminating light rays intersect at a common point on any surface of the transparent window, an angle between an outgoing illuminating light ray and a surface normal exceeds an angle between an incoming image ray and the surface normal such that a reflection of the outgoing illuminating light ray from said any surface is not within the field of view (FOV) of the panoramic camera.

2. The in vivo image capturing system of claim 1 wherein the panoramic camera comprises an entrance pupil, and wherein a single image plane in the panoramic camera captures a panoramic image of a subject surface outside the capsule.

3. An in vivo image capturing system according to claim 2 wherein the capsule comprises a panoramic annular lens having a concentric axis of symmetry and two refractive surfaces and two reflective surfaces configured to allow incoming light to pass through a first refractive surface into a transparent medium, to be reflected by a first reflective surface, then reflected by a second reflective surface, and then to exit the transparent medium through a second refractive surface.

4. An in vivo image capturing system according to claim 3, wherein the two reflective surfaces and the two refractive surfaces are conicoid surfaces of revolution, and wherein a conic constant of the first reflective surface is in a range of −0.6 to +2, where another conic constant of the second reflective surface is chosen to be less than that of the first.

5. An in vivo image capturing system according to claim 3, wherein each of the two reflective surfaces and the two refractive surfaces is one of a conicoid surface of revolution, a spheroidal surface, or an aspheroidal surface.

6. An in vivo image capturing system according to claim 2, wherein the capsule comprises a closed housing including the transparent window, and wherein the field of view (FOV) of the panoramic camera comprises a longitudinal field of view defined by a range of view angles relative to a longitudinal axis of the capsule and a latitudinal field of view defined by a panoramic range of azimuth angles about the longitudinal axis such that the panoramic camera can capture the panoramic image covering substantially a 360 deg latitudinal FOV and a longitudinal FOV ranging from some angle greater than 0 deg to another angle greater than 90 deg.

7. An in vivo image capturing system according to claim 6, wherein the capsule comprises a panoramic annular lens having a concentric axis of symmetry and two refractive surfaces and two reflective surfaces configured to allow incoming light to pass through a first refractive surface into a transparent medium.

8. An in vivo image capturing system according to claim 1, further comprising a data processor configured to generate a continuous image made up of multiple captured images.

9. An in vivo image capturing system according to claim 8, wherein the data processor is located outside the capsule.

10. The in vivo image capturing system of claim 1 wherein the reflector is configured to reflect the ray of light outside the capsule.

11. The in vivo image capturing system of claim 1 wherein several of the outgoing illuminating light rays pass from the light source into a material, reflect from a reflective surface of the material comprised in said reflector, and then pass to the exterior surface of the transparent window.

12. An in vivo image capturing system according to claim 1, further comprising:
a power source for providing power to the light source and the panoramic camera; and
a memory coupled to the panoramic camera to store at least one image captured by the panoramic camera.

13. A method for in vivo imaging with a camera encased within a capsule, comprising:
providing a capsule housing having a window at least partially transparent to electromagnetic radiation in a given wavelength range;
wherein the camera is a panoramic camera with a field of view exceeding 180 degrees;
ingesting said capsule by a patient;
emitting electromagnetic radiation in said given wavelength range through a first set of inner and outer transparent window surface regions of the window of said capsule housing;
detecting images from reflections of said electromagnetic radiation by a subject surface of said patient, through a second set of inner and outer transparent window surface regions of the window with an image sensor in the panoramic camera;
wherein the capsule comprises a reflector configured to reflect a ray of light from an illuminating light source, away from the panoramic camera;
wherein wherever incoming image rays and outgoing illuminating light rays intersect at a common point on any surface of the window, an angle between an outgoing illuminating light ray and a surface normal exceeds an angle between an incoming image ray and the surface normal such that a reflection of the outgoing illuminating light ray from said any surface is not within a field of view (FOV) of the panoramic camera.

14. A method according to claim 13, further comprising:
uploading the images to a computer for processing.

15. A method according to claim 14, wherein:
said uploading the images comprises retrieving the capsule housing and connecting the capsule to the computer.

16. A method according to claim 14, wherein:
said uploading the images comprises transmitting the images from the capsule to the computer.

17. A method according to claim 13, further comprising
performing compression on the images resulting from said detecting to produce compressed image data; and
uploading the compressed image data.

18. A method according to claim 17, further comprising
after said performing and before said uploading, storing the compressed image data in a memory in the capsule.

19. A method according to claim 13, further comprising
uploading the images with a wireless signal.

20. A method according to claim 13, further comprising
performing compression on the images resulting from said detecting, to produce compressed image data; and
uploading the compressed image data via a wireless communication signal.

21. A method according to claim 13, further comprising
performing compression on the images detected by the image sensor in the capsule to produce compressed image data;
storing the compressed image data in a memory in the capsule; and
uploading the compressed image data via a wireless communication signal.

22. A method according to claim 13 wherein:
at least a portion of said electromagnetic radiation passes from a light source comprised in the capsule into a material in the capsule, reflects from a reflective surface of the material comprised in said reflector, and then passes to an exterior surface of the window.

23. A method according to claim 13 further comprising generating a continuous image comprising multiple images resulting from said detecting.

24. A method according to claim 13, further comprising:
uploading image data from the image sensor to a receiver outside the patient.

25. An in vivo image capturing system comprising:
a capsule enclosing a camera, the capsule comprising a transparent window configured to pass light into the camera;
a light source enclosed within the capsule;

a reflector configured within the capsule to reflect at least one ray of light from the light source;

wherein wherever outgoing illuminating light rays after reflection by the reflector intersect with incoming image rays at a common point on a surface of the transparent window, an angle between an outgoing illuminating light ray reflected by the reflector and a surface normal exceeds an angle between an incoming image ray and the surface normal such that a reflection of the outgoing illuminating light ray from said surface is not within a field of view (FOV) of the camera.

26. The in vivo image capturing system of claim 25 wherein:
the reflector comprises another surface coated with a reflective coating that reflects said at least one ray of light from the light source.

27. The in vivo image capturing system of claim 26 wherein:
the reflective coating is a metal reflective coating.

28. The in vivo image capturing system of claim 26 wherein:
the reflective coating is a dielectric reflective coating.

29. The in vivo image capturing system of claim 25 wherein:
the field of view of the camera exceeds 180 degrees.

30. The in vivo image capturing system of claim 25 wherein:
the camera is panoramic; and
a single image plane in the camera is configured to capture a panoramic image of a subject surface outside the capsule.

31. The in vivo image capturing system of claim 25 wherein:
the reflector is configured to reflect said at least one ray of light away from the camera.

32. The in vivo image capturing system of claim 25 wherein:
the reflector is configured to reflect said at least one ray of light outside the capsule, through the transparent window.

33. A method for in vivo imaging with an ingestible capsule, the method comprising:
generating electromagnetic radiation at an illumination source in the ingestible capsule;
using a reflector within the ingestible capsule to reflect at least one ray of said electromagnetic radiation away from a camera in the ingestible capsule;
emitting through a transparent window of the ingestible capsule, at least one portion of said electromagnetic radiation including said at least one ray of said electromagnetic radiation; and
using an image sensor in the camera, to detect at least one image of a gastrointestinal tract, at least from reflections of said at least one portion outside the ingestible capsule that are received through the transparent window;
wherein wherever outgoing illuminating rays, after reflection by the reflector, intersect with incoming image rays at a common point on a surface of the transparent window, an angle between an outgoing illuminating ray reflected by the reflector and a surface normal exceeds an angle between an incoming image ray and the surface normal such that a reflection of the outgoing illuminating ray from said surface is not within a field of view (FOV) of the camera.

34. The method of claim 33 wherein:
the reflector comprises another surface coated with a reflective coating that reflects said at least one ray of said electromagnetic radiation from the illumination source.

35. The method of claim 34 wherein:
the reflective coating is a metal reflective coating.

36. The method of claim 34 wherein:
the reflective coating is a dielectric reflective coating.

37. The method of claim 33 wherein:
the field of view of the camera exceeds 180 degrees.

38. The method of claim 33 wherein:
said at least one image is a panoramic image detected in a single plane in the camera.

39. The method of claim 33 wherein:
the reflector is used to reflect said at least one ray of said electromagnetic radiation outside the ingestible capsule, through the transparent window.

40. An in vivo image capturing system comprising:
a capsule enclosing a camera, the capsule comprising a transparent window configured to pass light into the camera;
a light source enclosed within the capsule;
a reflector configured within the capsule to reflect at least one ray of light from the light source;
whereby the transparent window comprises a point P on an outer surface thereof, at which a ray A entering the capsule is captured at a largest field angle by an aperture of the camera, and the transparent window is adapted to refract the ray A at an angle $\alpha_2$ with respect to a surface normal;
wherein the reflector is positioned at a distance g measured:
(a) from an intersection of a line segment between the point P, at an angle $-\alpha_2$ with the surface normal, and an inner wall of the transparent window;
(b) to an apex of the reflector; and
such that wherever outgoing illuminating light rays after reflection by the reflector intersect with incoming image rays at the point P on the outer surface of the transparent window, an angle between an outgoing illuminating light ray reflected by the reflector and the surface normal exceeds $|\alpha_2|$.

41. The in vivo image capturing system of claim 40 further comprising:
a data processor configured to generate a continuous image made up of multiple captured images.

42. The in vivo image capturing system of claim 41 wherein:
the data processor is located outside the capsule.

43. The in vivo image capturing system of claim 40 wherein:
the reflector comprises at least one of a prism or a ring of triangular cross section.

44. The in vivo image capturing system of claim 40 wherein:
the reflector is configured to reflect a ray of light (B) from the light source, away from the camera, which is a panoramic camera, such that scattering of said ray (B) outside the capsule results in a scattered ray (B') entering a field of view of the camera.

45. The in vivo image capturing system of claim 40 wherein:
the camera is a panoramic camera; and
the reflector is configured to reflect one or more of the outgoing illuminating light rays away from the panoramic camera in a manner that prevents stray light from directly entering a lens without being scattered by a subject surface.

46. The in vivo image capturing system of claim 40 wherein:

the camera is a panoramic camera configured to capture a panoramic image of an environment surrounding the panoramic camera; and the panoramic image is captured on a single image plane.

47. The in vivo image capturing system of claim 40 wherein:

the capsule comprises a closed housing including the transparent window for passing light into the camera, which is a panoramic camera; and the panoramic camera is configured with a longitudinal field of view defined by a range of view angles relative to a longitudinal axis of the capsule and a latitudinal field of view defined by a panoramic range of azimuth angles about the longitudinal axis such that the panoramic camera can capture a panoramic image covering a 360 deg latitudinal FOV and a longitudinal FOV ranging from some angle greater than 0 deg to another angle greater than 90 deg.

48. The in vivo image capturing system of claim 40 wherein:

the camera is a panoramic camera which includes a panoramic annular lens;

the panoramic annular lens has a concentric axis of symmetry and includes two refractive surfaces and two reflective surfaces configured to allow incoming light to pass through a first refractive surface into a transparent medium.

49. A method for in vivo imaging with an ingestible capsule, the method comprising:

providing a capsule having a window at least partially transparent to electromagnetic radiation in a given wavelength range;

ingesting said capsule by a patient;

emitting electromagnetic radiation in said given wavelength range from said capsule;

detecting images from reflections of said electromagnetic radiation with an image sensor using a camera;

whereby the window comprises a point P on an outer surface, at which a ray A entering the capsule is captured at a largest field angle by an aperture of the camera, and the window is adapted to refract the ray A at an angle $\alpha_2$ with respect to a surface normal;

wherein a reflector is positioned at a distance g measured:
(a) from an intersection of a line segment between the point P, at an angle $-\alpha_2$ with the surface normal, and an inner wall of the window;
(b) to an apex of the reflector; and such that wherever outgoing illuminating light rays after reflection by the reflector intersect with incoming image rays at the point P on the outer surface of the window, an angle between an outgoing illuminating light ray reflected by the reflector and the surface normal exceeds $|\alpha_2|$.

50. The method of claim 49 further comprising:

performing compression on images resulting from said detecting, to produce compressed image data.

51. The method of claim 50 further comprising:

storing the compressed image data in a memory in the capsule.

52. The method of claim 50 further comprising:

uploading the compressed image data via a wireless signal.

53. The method of claim 49 wherein:

the reflector comprises at least one of a prism or a ring of triangular cross section.

54. The method of claim 49 wherein:

the camera is a panoramic camera; and the reflector is configured to reflect one or more of the outgoing illuminating light rays away from the panoramic camera in a manner that prevents stray light from directly entering a lens without being scattered by a subject surface.

* * * * *